(12) United States Patent
Grimm et al.

(10) Patent No.: US 12,179,184 B2
(45) Date of Patent: Dec. 31, 2024

(54) DEVICE AND METHOD FOR COMPENSATING SHORT-TERM PRESSURE OR VOLUME FLUCTUATIONS OF A MEDIUM IN A CONTINUOUS BIOPHARMACEUTICAL PROCESS

(71) Applicant: Sartorius Stedim Biotech GmbH, Goettingen (DE)

(72) Inventors: Christian Grimm, Goettingen (DE); Jochen Scholz, Goettingen (DE); Matthias Bode, Goettingen (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 784 days.

(21) Appl. No.: 17/419,572

(22) PCT Filed: Dec. 19, 2019

(86) PCT No.: PCT/EP2019/086443
§ 371 (c)(1),
(2) Date: Jun. 29, 2021

(87) PCT Pub. No.: WO2020/144044
PCT Pub. Date: Jul. 16, 2020

(65) Prior Publication Data
US 2022/0062842 A1    Mar. 3, 2022

(30) Foreign Application Priority Data
Jan. 7, 2019   (DE) ..................... 10 2019 100 209.5

(51) Int. Cl.
*B01J 3/04*    (2006.01)
*F16L 55/04*   (2006.01)

(52) U.S. Cl.
CPC ...... *B01J 3/046* (2013.01); *B01J 2219/00033* (2013.01); *B01J 2219/00162* (2013.01); *F16L 55/04* (2013.01)

(58) Field of Classification Search
CPC .............. B01J 3/046; B01J 2219/00162; B01J 2219/00033; F16L 55/04
See application file for complete search history.

(56) References Cited

U.S. PATENT DOCUMENTS 2,337,771 A     12/1943  Roberts
3,878,867 A *   4/1975   Dirks .................... F16L 55/054
                                                           138/30

(Continued)

FOREIGN PATENT DOCUMENTS

CH    353341 A     4/1961
DE    2653567 A1   6/1977

(Continued)

OTHER PUBLICATIONS

International Search Report issued in International Application No. PCT/EP2019/086443, issued Apr. 24, 2020, 2 pages.

*Primary Examiner* — Lessanework Seifu
(74) *Attorney, Agent, or Firm* — Dilworth IP, LLC (57) ABSTRACT

A device for compensating short-term pressure or volume fluctuations of a medium in a continuously managed biopharmaceutical process including a receiving space in fluid communication with a process line through which a medium flows, an equalizing space, which is separated from the receiving space by a deflectable element, and a counter-pressure mechanism in the equalizing space for applying a counter-pressure to the deflectable element towards the receiving space. A method of compensating short-term pressure or volume fluctuations of a medium in a continuously managed biopharmaceutical process including providing a receiving space in fluid communication with a process line (Continued)

through which a medium flows, receiving an excess amount of the medium flowing into the receiving space, charging an energy storage device by the medium flowing into the receiving space, and expelling at least part of the excess amount if the pressure or flow rate falls below a set amount.

17 Claims, 4 Drawing Sheets

(56) References Cited

U.S. PATENT DOCUMENTS

| | | | | |
|---|---|---|---|---|
| 4,274,446 | A | * | 6/1981 | Zahid .................. F15B 1/14 220/721 |
| 4,307,753 | A | * | 12/1981 | Dryer .................. F16L 55/053 138/30 |
| 5,038,828 | A | * | 8/1991 | Fonser .................. F15B 1/12 138/30 |
| 5,797,430 | A | | 8/1998 | Becke et al. |
| 6,675,835 | B2 | * | 1/2004 | Gerner .................. G01N 30/36 96/10 |
| 9,133,433 | B2 | | 9/2015 | Vogel et al. |
| 9,272,526 | B2 | | 3/2016 | Ando |
| 10,480,704 | B2 | | 11/2019 | Yoshida et al. |
| 2016/0114950 | A1 | | 4/2016 | Baud |
| 2018/0306368 | A1 | | 10/2018 | Yoshida et al. |
| 2019/0099539 | A1 | * | 4/2019 | Los .................. A61M 1/267 |

FOREIGN PATENT DOCUMENTS

| | | |
|---|---|---|
| DE | 3441249 A1 | 5/1985 |
| DE | 4318553 A1 | 12/1994 |
| DE | 19814835 A1 | 10/1999 |
| DE | 10226204 A1 | 12/2003 |
| DE | 102006046457 A1 | 4/2008 |
| DE | 112016002359 T5 | 2/2018 |
| FR | 794187 A | 2/1936 |

* cited by examiner

DEVICE AND METHOD FOR COMPENSATING SHORT-TERM PRESSURE OR VOLUME FLUCTUATIONS OF A MEDIUM IN A CONTINUOUS BIOPHARMACEUTICAL PROCESS

FIELD OF THE INVENTION

The invention relates to a device and a method for compensating short-term pressure or volume fluctuations of a medium in a continuously managed biopharmaceutical process.

BACKGROUND

A multitude of processes such as cell separation (e.g. by deep bed filtration), sterile filtration, chromatography, virus inactivation, virus filtration and cross-flow filtration are known from biopharmaceutics. All of these processes constitute basic operations that are interconnected on a regular basis to form different overall processes. A distinction is made here between batch processes (batch mode), in which the respective intermediate product is collected in a container after each process step or each basic operation, and continuous processes, in which the medium is made available continuously and "on demand". A continuous process here should also be understood to include a quasi-continuous process, in which intermediate buffering and/or switching over between several alternative flow paths takes place in individual process steps, but still a steady stream of product is generated.

When a production is carried out in a continuous process, special precautionary measures need to be taken to interconnect individual process steps. In the individual steps, the volume flow rate or the pressure in the connecting line system may fluctuate heavily for principle-related reasons, e.g. in the case of filtration. Special events, e.g. switching over from one filtration unit to another in the event of a filter being blocked, also lead to process conditions that fluctuate heavily for a short time. However, since many process steps are designed for a stationary condition, a short stop and subsequent resumption ("start-up") of the process is associated with fluctuating process conditions and thus with a fluctuating output quality.

To counteract this behavior, buffer tanks are usually provided after certain substeps or after the individual basic operations, which can temporarily store a certain volume in order to compensate fluctuations in this way. However, a significant disadvantage of using such buffer tanks is that an active element, in particular in the form of a pump, is required in each case in order to maintain the volume flow and/or the pressure in the system, if necessary. This in turn requires a high degree of automation.

SUMMARY

The object of the invention is to provide a compensation of short-term pressure or volume fluctuations in a continuously managed biopharmaceutical process in a simple and effective way.

This object is achieved by a device having the features of claim 1 and by a method having the features of claim 16. Advantageous and expedient further developments of the device according to the invention and of the method according to the invention are indicated in the associated dependent claims.

The device according to the invention for compensating short-term pressure or volume fluctuations of a medium in a continuously managed biopharmaceutical process includes a receiving space in fluid communication with a process line through which a medium flows, for temporarily storing an excess amount of the medium flowing into the receiving space. The device according to the invention further includes an equalizing space, which is separated from the receiving space by a deflectable, more particularly flexible and elastically deflectable, element, and a counter-pressure means arranged in the equalizing space for applying a counter-pressure to the deflectable element towards the receiving space. All media-contacting components of the device according to the invention are designed as disposable components.

The invention is based on the finding that in a continuously managed biopharmaceutical process, the losses of quality caused by short-term fluctuations in pressure or volume can be avoided by not only providing collection containers for the medium, but at the same time taking measures to automatically return the medium collected after a pressure surge or an excess of volume to the process again as soon as conditions to the contrary exist. The device according to the invention thus allows volume fluctuations to be compensated if necessary, and the system pressure can be kept largely constant so that the process conditions remain stable without this necessitating more elaborate solutions involving additional pumps in the process lines. In particular in the case of incompressible media, process reliability is increased, since any sudden, long-lasting increase in pressure can also be absorbed and the rise in pressure in the system proceeds more slowly or is reduced. This also extends the time window for an emergency cutout of the process.

According to a special aspect of the invention, the counter-pressure means—from an abstract view—comprises an energy storage device which is charged by the medium flowing into the receiving space. The energy storage device may be implemented by, e.g., an elastically deformable element, such as a foamed material or a spring element. Under the appropriate conditions, the stored energy is then made use of to expel the medium from the receiving space again. In the simplest case, no external energy is then required at all to compensate the pressure or volume fluctuations.

A diaphragm is particularly suitable as a deflectable element. The clamping of an elastically deflectable diaphragm has already stood the test in other technical fields, for example for opening or closing a valve seat in the case of valves. In the device according to the invention, the diaphragm serves to increase the volume of the receiving space at the expense of the volume of the equalizing space for a short time, thereby building up a counter-pressure in the equalizing space. As a component in contact with the medium, the diaphragm is designed as a sterilized disposable diaphragm.

A further development of the invention provides for the use of a semipermeable diaphragm or, more generally, a semipermeable deflectable element. In addition to the compensation of pressure or volume fluctuations, this allows the device according to the invention to be additionally used to achieve a degassing of the medium, which is significant in particular in filling processes.

In specific embodiments, a receiving body, in particular a balloon, or an expansible tube section may also be employed as the deflectable element. The receiving body or the tube section then constitutes essentially the entire receiving space and is accordingly designed as a disposable component.

It is, in principle, possible to provide the receiving space for the medium to be temporarily stored in a reusable container. In order to avoid contact of the medium with the container wall, which would require cleaning or sterilization before and after the process, the receiving space in the container may be delimited at least in part by a disposable insert, for example a suitable film, i.e. those areas of the receiving space which are not already formed by a disposable diaphragm or the like are delimited by the disposable insert.

A gas under positive pressure (above atmospheric pressure) may be provided to serve as a counter-pressure means in the equalizing space, i.e. the equalizing space is filled with a pressurized gas. Basically, it is also possible to simply place a liquid or a solid body in the receiving space, which then exerts a counter-pressure by its weight on the diaphragm towards the receiving space. As already indicated above, an elastic solid body is suitable in particular for use as a solid body, exerting an additional counter-pressure through its deformation.

In a simple embodiment, the equalizing space with the counter-pressure means located therein is closed so that the latter cannot escape (in particular in the case of compressed gas). In a more complex embodiment, a connection opening into the equalizing space is provided for a supply or a withdrawal of fluid. This connection can be used to change the amount of fluid or its pressure within the equalizing space when required.

A constant pressure source may, for example, be connected to the connection to ensure a uniform pressure in the equalizing space, or a syringe with a syringe driver.

The connection opening into the equalizing space also provides the option of using a controller for closed-loop control of the counter-pressure in the receiving space as a function of measured pressure or volume fluctuations. In this case, the counter-pressure is automatically adjusted to the respective conditions.

When selecting a housing or container for the device according to the invention, tried and tested disposable housing designs may be made use of. In particular, the receiving space and the equalizing space may be arranged in a disposable filter capsule housing or in a disposable filter cartridge housing. Such housings have the advantage that their sterilizability, pressure resistance and further parameters are precisely known. In addition, at least one of the existing connections of the known housing design can be connected to the process line and/or be utilized for a supply or a withdrawal of fluid to or from the equalizing space when applied in accordance with the invention.

In a further embodiment of the device according to the invention, the receiving space and the equalizing space are arranged in a housing, preferably a cylinder, and are separated by a piston which is displaceable in the housing and sealed from the housing. The piston can be displaced against a resistance in one direction by the medium entering the receiving space and in the other direction for expelling the medium.

For this purpose, the piston can be urged towards the receiving space by a (mechanical, pneumatic or electromagnetic) force, in particular by an adjustable or variable force.

The device according to the invention need not necessarily be arranged at a branch-off of a process line. A special embodiment of the invention provides for a medium inlet into the receiving space and a medium outlet from the receiving space, the receiving space being surrounded by the equalizing space so that the device can be arranged in a through-flow. That is, the medium flows through the receiving space and can expand it radially outward if needed, with the counter-pressure means in the equalizing space building up a counter-pressure directed radially inward.

In this embodiment, the receiving space between the inlet and the outlet may be formed, in particular, by an elastically expansible, disposable tube section surrounded by a rigid or flexible container, in particular a sleeve, which is sturdier than the tube section. The expansible tube section can widen when the pressure is too high, and can thereby absorb more volume for a short time. The counter-pressure means arranged in the equalizing space between the tube and the rigid container or the sturdy sleeve makes sure that the tube section will contract again under conditions to the contrary, if necessary to a smaller diameter than under normal conditions, in order to smooth out any pressure fluctuations.

The invention also provides a method of compensating short-term pressure or volume fluctuations of a medium in a continuously managed biopharmaceutical process, preferably using a device according to the invention, the method comprising the following steps:

providing a receiving space in fluid communication with a process line through which a medium flows;

receiving, in the event of an excess pressure or an excess volume in the process line, an excess amount of the medium flowing into the receiving space;

charging an energy storage device by the medium flowing into the receiving space; and expelling at least part of the received excess amount of the medium out of the receiving space in the event that the pressure falls below a set pressure range or the flow rate falls below a set flow rate range by conversion of the energy stored in the energy storage device.

As discussed above, the energy storage device may be additionally supplied with energy from outside, for example by connecting the receiving space to a pressure source.

According to a further development of the method according to the invention, the energy input is closed-loop controlled by means of a controller as a function of measured pressure or volume fluctuations. In this way, an optimum equalization is continually possible without the need for manual intervention.

BRIEF DESCRIPTION OF THE DRAWINGS

Further features and advantages of the invention will be apparent from the description below and from the accompanying drawings, to which reference is made and in which.

DETAILED DESCRIPTION

FIGS. 1 to 4 illustrate different variants of a first embodiment of a device 10 for compensating short-term pressure or volume fluctuations of a medium in a continuously managed biopharmaceutical process. The device 10 comprises a container 12 having a bottom part 14 and a top part 16. A film 20 covering the inner wall or walls of the bottom part 14 and a flexible diaphragm 22 arranged thereabove are clamped between the bottom part 14 and an edge 18 of the top part 16, for example with the aid of quick-action clamps. The diaphragm 22 functionally divides the container 12 into a receiving space 24 (below the diaphragm 22) and an equalizing space 26 (above the diaphragm 22). The receiving space 24 is connected to a process line through which a medium flows during a continuous process. One single connection 28 may be provided, through which medium can flow both into and out of the receiving space 24, or two separate connections are provided, which may be equipped with check valves, where required, so that medium can flow into the receiving space 24 only through one connection and medium can flow out of the receiving space 24 only through the other connection. The film 20 has corresponding openings at the connection 28 or at the connections, the openings being sealed with respect to the bottom part 14.

Figure 1:
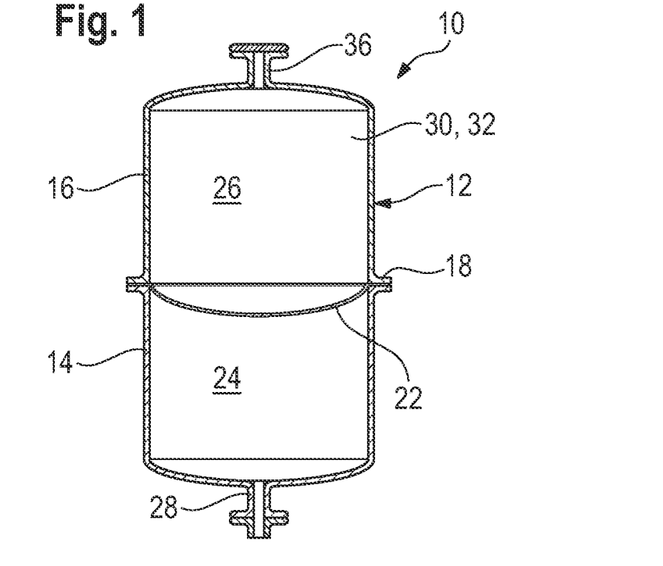
FIG. 1 shows a schematic diagram of a device according to the invention for compensating short-term pressure or volume fluctuations of a medium in a continuously managed biopharmaceutical process according to a first embodiment.
Figure 2:
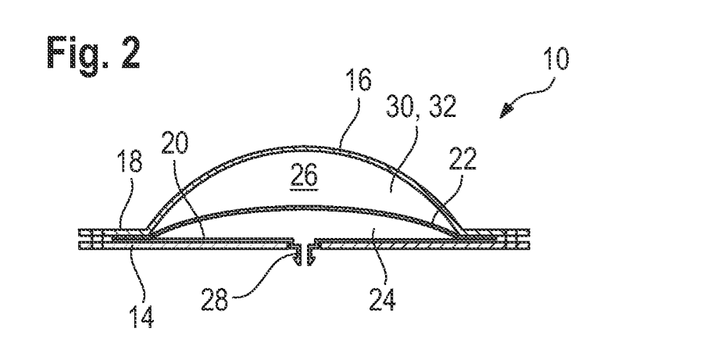
FIG. 2 shows a schematic sectional view of a first variant of the first embodiment.

The equalizing space 26, which according to FIG. 1 is closed, contains a counter-pressure means 30 which exerts a counter-pressure on the diaphragm 22 when the latter is deflected towards the equalizing space 26. In principle, this can be achieved in various ways. The equalizing space 26 may be completely or almost completely filled with a fluid 32, in particular gas under an overpressure (pressure above atmospheric pressure). Alternatively or additionally, an elastic solid body 34, e.g. a foamed material, may be arranged in the equalizing space 26, as in the variant shown in FIG. 4. The equalizing space 26 may also contain a solid or a liquid having a specific minimum mass, the force of gravity of which presses on the diaphragm 22.

While those components of the device 10 that contact the medium, such as, e.g., the diaphragm 22, are pre-sterilized disposable components made of plastic, the other components of the device 10, in particular the container 12, may be reusable components made of stainless steel or an easy-to-clean plastic material. Of course, the other components or some of them may also be designed as disposable components.

If, while carrying out the continuous process, an excess pressure (exceeding a set pressure range) or an excess volume (exceeding a set flow rate range) occurs in the process line through which the medium flows, a corresponding excess quantity of the medium is pressed into the receiving space 24 of the device 10. This causes the diaphragm 22 to be deflected, in this case upward, against the resistance of the counter-pressure means 30 located in the equalizing space 26. The counter-pressure means 30 can be understood as an energy storage device that is (further) charged by the medium flowing into the receiving space 24.

The counter-pressure means 30 applies a counter-pressure via the diaphragm 22 to the medium temporarily stored in the receiving space 24, the counter-pressure means 30 and the diaphragm 22 being coordinated in such a way that the temporarily stored medium is expelled from the receiving space 24 again, ideally as soon as the pressure falls below the set pressure range or the flow rate falls below the set flow rate range in the process line. The energy required for expelling the medium from the receiving space 24 originates from the counter-pressure means 30 serving as an energy storage device, i.e. the energy storage device discharges again.

Figure 3:
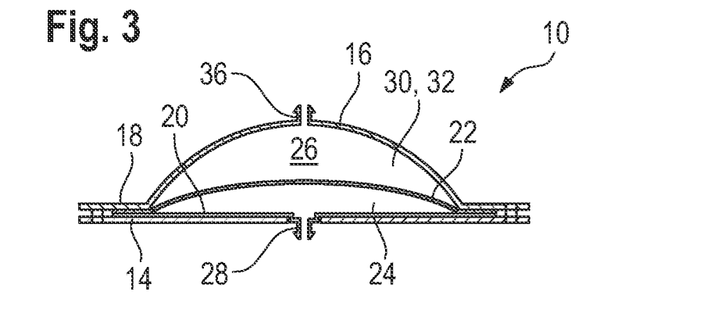
FIG. 3 shows a schematic sectional view of a second variant of the first embodiment.
Figure 4:
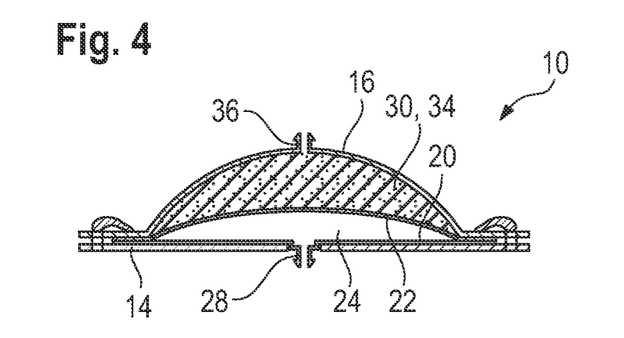
FIG. 4 shows a schematic sectional view of a third variant of the first embodiment.

In the variants shown in FIGS. 1, 3 and 4, a connection 36 opening into the equalizing space 26 is additionally provided on the container 12. A fluid 32 (gas or liquid) can flow into or out of the equalizing space 26 through this connection 36. This allows the counter-pressure on the diaphragm 22 to be adjusted as desired, e.g. by means of a constant pressure source or a syringe with a syringe driver. With the aid of a suitable controller, an automatic closed-loop control of the counter-pressure as a function of the measured pressure or volume fluctuations in the system is also possible.

Where required, the diaphragm 22 selected may be a semipermeable diaphragm that is arranged to be permeable to gas towards the equalizing space 26. In this case, the device 10 may additionally be made use of for degassing the medium, since gas contained in the medium in the container escapes from the receiving space 24 into the equalizing space 26 through the diaphragm.

Figure 5:
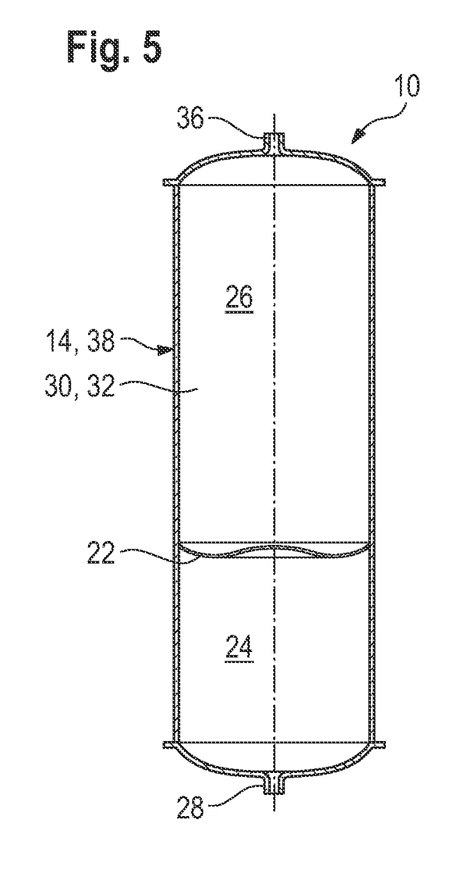
FIG. 5 shows a schematic sectional view of a compensating device according to a first variant of a second embodiment of the invention.
Figure 6:
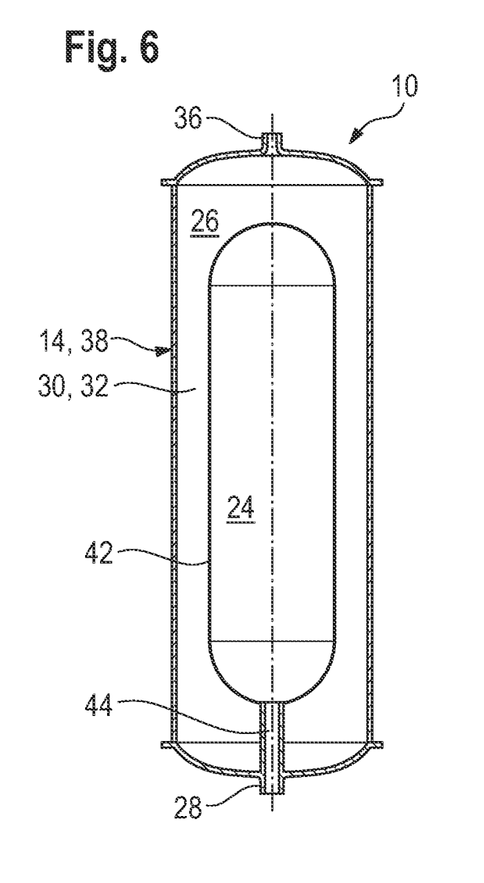
FIG. 6 shows a schematic sectional view of a second variant of the second embodiment.
Figure 7:
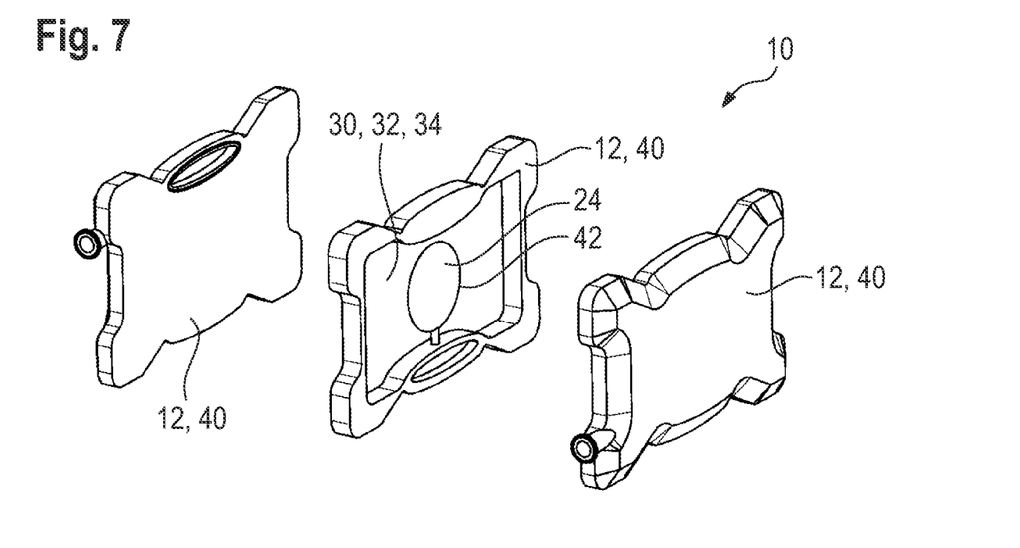
FIG. 7 shows an exploded view of a third variant of the second embodiment.

FIGS. 5, 6 and 7 show three variants of a second embodiment of the compensating device 10, in which the receiving space 24 and the equalizing space 26 are each housed in a container 12 in the form of a sterilized disposable plastic housing, the basic form of which is known per se. In the first case, the housing 38 of a substantially cylindrical disposable filter capsule (FIGS. 5 and 6) is used for the container 12; in the second case, the housing 40 of a disposable filter cartridge (FIG. 7) is used.

FIG. 5 shows a first variant of the second embodiment. Here, a flexible disposable diaphragm 22 is sealed in, glued in, welded in or the like between a lower connection 28 and one or two upper connections 36 of the filter capsule housing 38, so that the filter capsule housing 38 is divided into a receiving space 24, in this case below the diaphragm 22, and an equalizing space 26, in this case above the diaphragm 22. In this case, the lower connection 28 of the filter capsule housing 38 is used as a connection for the medium supply and discharge, while the upper connection 36 or, if applicable, one of the upper connections 36, is employed for the supply and, if applicable, discharge of a fluid 32 as the counter-pressure means 30. Any further connections of the filter capsule housing 38 remain closed during operation.

In the variant shown in FIG. 6, instead of the diaphragm 22, a sterilized disposable receiving body 42, here in the form of a flexible balloon, is accommodated in the filter capsule housing 38, which serves as the container 12. The single opening 44 of the receiving body 42 is coupled to the medium connection 28 and sealed such as to prevent any medium from entering the remaining space of the filter capsule housing 38. The interior of the receiving body 42 serves as a receiving space 24 for temporarily storing an excess of medium; the remaining space of the filter capsule housing 38, which may have one or more further connections 36, serves as an equalizing space 26, as described above.

In all variants of the second embodiment, the basic options for selecting the counter-pressure means 30 and the fundamental operating mode of the device 10, including the options for adjusting the counter-pressure in the equalizing space 26, are the same as those for the first embodiment.

FIG. 7 illustrates a third variant of the second embodiment of the compensating device 10. Here, the container 12 is provided in the form of the housing 40 of a cuboid filter cartridge with a receiving body 42 contained therein. The receiving body 42 is connected to the process line and adjusts its dimensions according to its contents (like the balloon in the second variant of the second embodiment). The closed equalizing space 26 surrounding the receiving body 42 contains a counter-pressure means 30, which applies a counter-pressure to the receiving body 42 as the latter expands towards the equalizing space 26. Basically, as in the embodiments and variants already described, this can be achieved in different ways. The equalizing space 26 can be completely or almost completely filled with a fluid 32, in particular gas under positive pressure (pressure above atmospheric pressure). Alternatively or additionally, an elastic solid body 34, e.g., a foamed material, may be arranged in the equalizing space 26. Techniques for adjusting or controlling the counter pressure may also be employed.

A special feature of all variants of the second embodiment is the high process reliability. Even in the event of leakage of the diaphragm 22 or the receiving body 42, the sterilized disposable housing 38, 40 of the filter capsule or, respectively, of the filter cartridge will keep the medium sterile, and the process will remain closed, i.e., no medium will exit the process in an uncontrolled manner.

Figure 8:
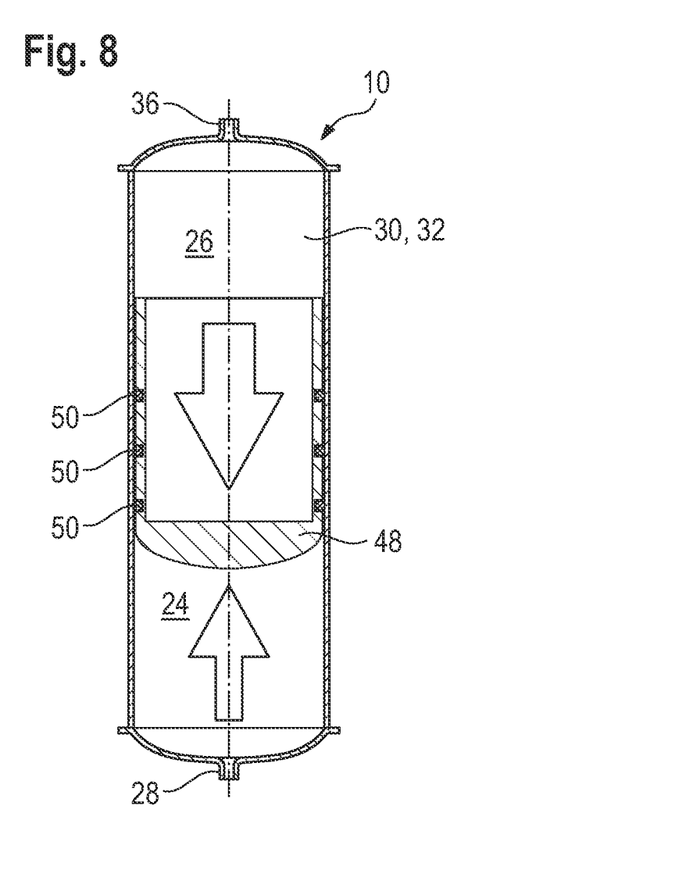
FIG. 8 shows a schematic sectional view of a compensating device according to a third embodiment of the invention.

FIG. 8 illustrates a third embodiment of the compensating device 10. Here, the container 12 is provided in the form of a cylinder 46 with a piston 48 displaceable therein as the counter-pressure means 30. The piston 48, here in interaction with a plurality of sealing elements 50, separates the cylinder space into a receiving space 24 and an equalizing space 26 as in the embodiments described above. The piston 48 can be displaced towards the receiving space 24 and back. The displacement of the piston 48 can either be controlled solely by the medium entering the receiving space 24 and the weight of the piston 48 acting against it, or the piston 48 is "pretensioned" or actively driven towards the receiving space 24. To this end, a fluid can be pumped into the equalizing space through a connection 36, an electromagnetic force or a spring force or other mechanical force can be applied to the piston 48, or any other of the techniques as described earlier for adjusting or controlling the counter-pressure can be employed.

Figure 9:
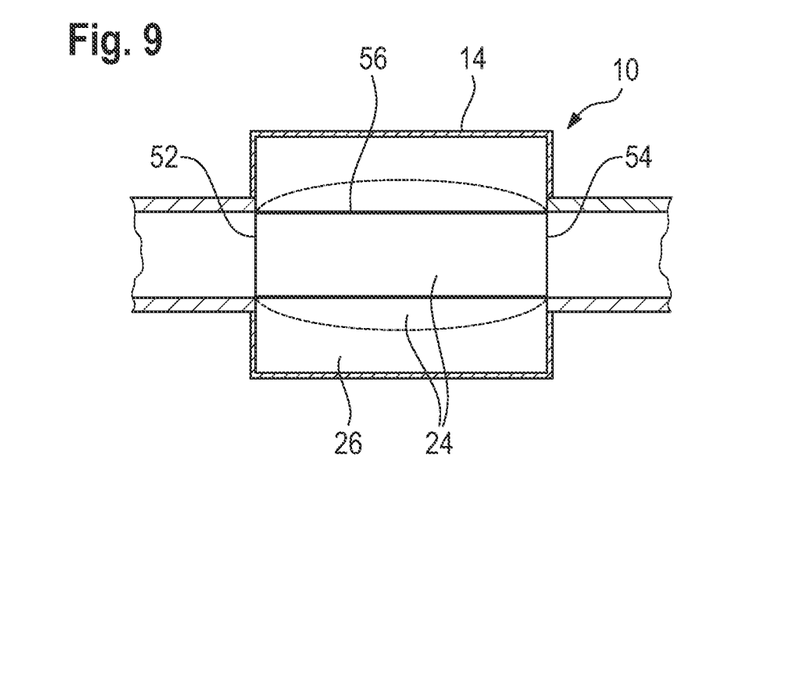
FIG. 9 shows a schematic sectional view of a compensating device according to a fourth embodiment of the invention.

Unlike the embodiments described so far, the fourth embodiment of the compensating device 10 shown in FIG. 9 is arranged directly in the flow, rather than at a branch-off of a process line. This means that the medium the pressure or volume fluctuations of which are to be compensated enters the device 10 through an inlet 52 on one side and exits through an outlet 54 on another side.

The compensating device 10 may be integrated in a main line or a secondary line. The two ends of the device 10 may, for example, be formed as connecting ends that fit a common tri-clamp connector, as in the variant shown in FIG. 10.

Figure 10:
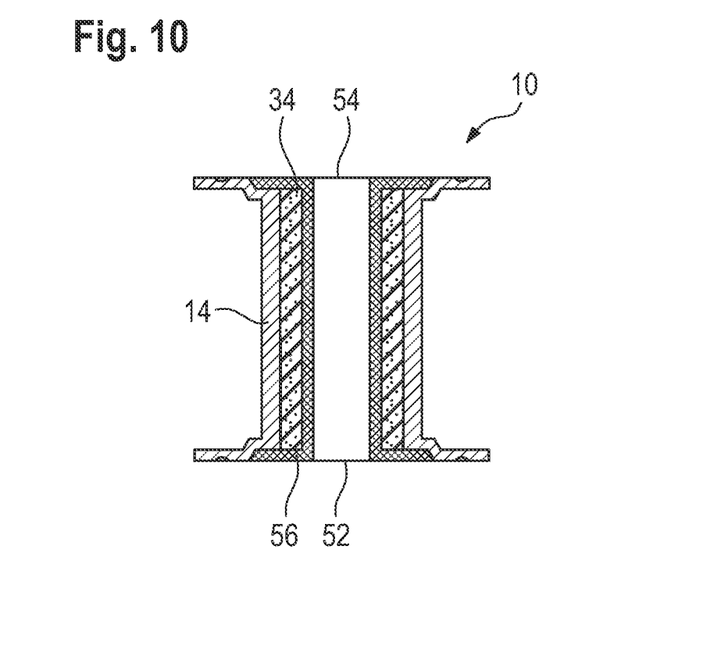
FIG. 10 shows a schematic sectional view of a variant of the fourth embodiment.

Between the inlet 52 and the outlet 54, the process line is formed as an elastically expansible, sterilized, disposable tube section 56, e.g., made from rubber. This portion is surrounded by a sturdy and tight container 12, which need not necessarily be designed as a disposable container.

The tube section 56 can expand when there is an excess pressure in the process line or when there is an excess volume, thus acting as an additional receiving space 24 for the medium. The area between the outer wall of the expansible tube section 56 and the inner wall of the container 12 acts as an equalizing space 26. The container 12 may include an outer connection 36. Providing and, if required, adjusting or controlling the counter-pressure may again be achieved in a variety of ways, as described above.

Rather than a rigid container 12, a hard or flexible sleeve, for example made from a hard or strong plastic such as PE, can also serve as the container 12 and be arranged around the expansible tube section 56 and fastened tightly to it. However, the sleeve should be more rigid or less expansible than the tube section 56 to allow a sufficient counter-pressure to be provided. The cavity between the expansible hose section 56 and the sleeve then constitutes the equalizing space 26.

Any pressure fluctuations can thus be smoothed by widening or narrowing the tube section 56 and therefore by a change in volume.

Just as in the first embodiment, in all other embodiments the diaphragm 22 or the respective deflectable element (receiving body 42, expansible tube section 56, etc.) that separates the receiving space 24 from the equalizing space 26 can be configured as a semipermeable element that is gas-permeable towards the equalizing space 26 to allow degassing of the medium in the device 10.

LIST OF REFERENCE NUMBERS 10 device
12 container
14 bottom part
16 top part
18 edge
20 film
22 diaphragm
24 receiving space
26 equalizing space
28 connection
30 counter-pressure means
32 fluid
34 elastic solid body
36 connection
38 filter capsule housing
40 filter cartridge housing
42 receiving body
44 opening
46 cylinder
48 piston
50 sealing elements
52 inlet
54 outlet
56 tube section

The invention claimed is:

1. A device for compensating short-term pressure or volume fluctuations of a medium in a continuously managed biopharmaceutical process, comprising:
  a receiving space in fluid communication with a process line through which a medium flows, for temporarily storing an excess amount of the medium flowing into the receiving space;
  an equalizing space, which is separated from the receiving space by a deflectable element;
  a connection opening into the equalizing space for a supply or a withdrawal of fluid, wherein a constant pressure source or a syringe with a syringe driver is connected to the connection;
  a counter-pressure device arranged in the equalizing space for applying a counter-pressure to the deflectable element towards the receiving space; and a controller for closed-loop control of the counter-pressure in the equalizing space as a function of measured pressure or volume fluctuations, wherein all media-contacting components of the device are designed as disposable components.

2. The device according to claim 1, wherein the counter-pressure device comprises an energy storage device which is charged by the medium flowing into the receiving space.

3. The device according to claim 1, wherein the deflectable element is a diaphragm.

4. The device according to claim 1, wherein the deflectable element is a receiving body.

5. The device according to claim 1, wherein the deflectable element is semipermeable to gas.

6. The device according to claim 1, wherein the receiving space is arranged in a reusable container and is delimited at least in part by a disposable insert.

7. The device according to claim 1, wherein the counter-pressure device comprises a gas under positive pressure and/or a liquid and/or an elastic solid body.

8. The device according to claim 1, wherein the receiving space and the equalizing space are arranged in a housing having connections, wherein at least one of the connections of the housing is connected to the process line and/or at least one of the connections of the housing is the connection for the supply or the withdrawal of the fluid into or from the equalizing space.

9. The device according to claim 1, wherein the receiving space and the equalizing space are arranged in a housing, and are separated by a piston which is displaceable in the housing and sealed from the housing.

10. The device according to claim 9, wherein the piston is urged towards the receiving space by a force.

11. The device according to claim 1, further comprising a medium inlet into the receiving space and a medium outlet from the receiving space, the receiving space being surrounded by the equalizing space so that the device can be arranged in a through-flow.

12. The device according to claim 11, wherein the receiving space between the inlet and the outlet is formed by an elastically expansible, disposable tube section and is surrounded by a rigid or flexible container which is sturdier than the tube section.

13. The device according to claim 4, wherein the receiving body is a balloon, or an expansible tube section which constitutes an entirety of the receiving space.

14. The device according to claim 9, where the housing is a cylinder.

15. The device according to claim 8, further comprising a disposable filter capsule or a disposable filter cartridge in the housing.

16. The device according to claim 10, wherein the force is an adjustable or variable force.

17. A method of compensating short-term pressure or volume fluctuations of a medium in a continuously managed biopharmaceutical process, using a device with a receiving space in fluid communication with a process line through which a medium flows for temporarily storing an excess amount of the medium flowing into the receiving space, an equalizing space which is separated from the receiving space by a deflectable element, and a counter-pressure device arranged in the equalizing space for applying a counter-pressure to the deflectable element towards the receiving space, wherein all media-contacting components of the device are designed as disposable components, the method comprising steps of:

providing the receiving space in fluid communication with the process line through which the medium flows;

receiving, in an event of an excess pressure or an excess volume in the process line, the excess amount of the medium flowing into the receiving space;

charging an energy storage device by the medium flowing into the receiving space; and expelling at least part of the received excess amount of the medium out of the receiving space in the event that a pressure falls below a set pressure range or a flow rate falls below a set flow rate range by conversion of energy stored in the energy storage device, wherein the energy storage device is additionally supplied with energy from outside, wherein an energy input is closed-loop controlled by a controller as a function of measured pressure or volume fluctuations.

* * * * *